United States Patent [19]

Mallen et al.

[11] Patent Number: 5,288,544
[45] Date of Patent: Feb. 22, 1994

[54] NON-LINTING, ANTI-STATIC SURGICAL FABRIC

[75] Inventors: Ted A. Mallen, Chattanooga; Doyle B. Word, Cleveland, both of Tenn.

[73] Assignee: Intera Company, Ltd., Cleveland, Tenn.

[21] Appl. No.: 662,515

[22] Filed: Feb. 28, 1991

Related U.S. Application Data

[63] Continuation of Ser. No. 427,375, Oct. 27, 1989, abandoned, which is a continuation of Ser. No. 278,468, Dec. 1, 1988, abandoned, which is a continuation of Ser. No. 924,866, Oct. 30, 1986, abandoned.

[51] Int. Cl.$^5$ .................................................. D03D 3/00
[52] U.S. Cl. ..................................... 428/224; 128/849;
428/225; 428/257; 428/285; 428/288; 428/408; 428/913
[58] Field of Search ............... 428/253, 257, 285, 408, 428/913, 288, 258, 259, 224, 225; 128/849

[56] References Cited

U.S. PATENT DOCUMENTS

| | | | |
|---|---|---|---|
| 3,008,215 | 11/1961 | Pitts | 28/81 |
| 3,288,175 | 11/1966 | Valko | 139/425 |
| 3,582,448 | 6/1971 | Okuhashi et al. | 161/87 |
| 3,586,597 | 6/1971 | Okuhashi | 161/87 |
| 4,083,124 | 4/1978 | Michalak | 36/7.1 R |
| 4,398,277 | 8/1983 | Christiansen et al. | 361/220 |
| 4,420,529 | 12/1983 | Westhead | 428/257 |
| 4,606,968 | 8/1986 | Thornton et al. | 422/257 |
| 4,647,495 | 3/1987 | Kanayama et al. | 428/257 |
| 4,672,005 | 6/1987 | Dyer | 428/474.4 |

FOREIGN PATENT DOCUMENTS

| | | |
|---|---|---|
| 2006725 | 1/1970 | France . |
| 2131066 | 10/1972 | France . |

*Primary Examiner*—James J. Bell
*Attorney, Agent, or Firm*—Oblon, Spivak, McClelland, Maier & Neustadt

[57] ABSTRACT

The present invention is directed to operating fabric articles comprising a synthetic substrate which has been treated to render it absorbent to aqueous media and an anti-statically effective amount of a conductive fiber.

13 Claims, No Drawings

NON-LINTING, ANTI-STATIC SURGICAL FABRIC

This application is a continuation of application Ser. No. 07/427,375, filed on Oct. 27, 1989, now abandoned, which is a continuation of Ser. No. 07/268,468, filed on Dec. 1, 1988, now abandoned, which is a continuation of Ser. No. 06/924,866, filed on Oct. 30, 1986, now abandoned.

BACKGROUND OF THE INVENTION

1. Field of the Invention

The present invention relates to synthetic fabric articles having a high affinity for aqueous media, very low linting characteristics and electrical conductivity so as to eliminate static electric charges. These fabric articles find particular applications in the form of surgical toweling, drapes, gowns, and wash cloths, for example, which are used in hospital operating rooms or where standards require.

2. Description of the Background

The fabric articles of the present invention have particular utility in hospital operating rooms where there is a need for highly absorbent fabric articles which are non-linting and essentially free of static electricity. Up to the present time it has not been possible to produce non-linting, static-free fabric articles from synthetic fibers which can be used in hospital operating rooms, and especially the toweling used in the operating rooms. There are several significant properties of synthetic fibers which render them unsuitable for such use. The first is the fact that fabric prepared from synthetic fibers is generally hydrophobic and cannot absorb aqueous media. Thus, a towel prepared from a synthetic fiber would not absorb blood, water or other aqueous media and thus would be essentially useless in the hospital operating room.

Second, synthetic fabrics have a tendency to develop static electrical charges during the drying cycle of the laundering process. Static electricity is normally generated when two different materials are rubbed together. If the resulting charges are retained and accumulated, a measurable potential is generated. If the material is a dielectric, charge builds up to the point where clinging and sparking may occur. While such static charges are inconvenient to the general consuming public and in other applications, the static charge in the hospital operating room would be dangerous since such operating rooms typically have elevated concentrations of oxygen and other flammable gases which could be ignited by the static charge. Thus, hospitals have been restricted to the use of cotton for the toweling which is employed in the hospital operating room since cotton is both highly absorbent and essentially free of static electrical charges. However, cotton toweling has a tendency to lint. Many believe it is the lint from the toweling used in the operating room which is the source of from 80% to 90% of the post-operative infections. Thus, hospitals have long sought alternatives to cotton toweling for use in the hospital operating room so as to reduce or eliminate lint as a source of potential infection.

Synthetic fabrics having useful absorbent properties are known. U.S. Pat. No. 4,275,105 discloses a stabilized rayon web which can be fabricated into textile articles. The stabilized rayon web shows no particulate discharge (lint or the like). U.S. Pat. No. 4,433,026 discloses a cloth-like three-layer laminate material in which the outer layers are made of polyester continuous filament yarn and the middle layer is made of an expanded polytetrafluoroethylene film. This laminate material is essentially lint-free and can be repeatedly laundered without delamination.

Techniques as also known for preventing the buildup of static electricity in the operating room environment. For example, U.S. Pat. No. 4,398,277 discloses a fabric strap containing conductive fibers to control the electrostatic charge accumulation on the body of an individual. The individual is grounded by means of a grounding wire connected to the fabric strap. U.S. Pat. No. 4,083,124 discloses a protective shoe covering incorporating a flexible grounding strap to prevent static buildup while walking in the operating room.

In addition to specific articles worn by a person in the operating room, several electrically conductive textile materials are also known. U.S. Pat. No. 3,958,066 discloses synthetic polymer fibers coated with a powdered metal oxide. U.S. Pat. No. 3,288,175 discloses a fabric having a continuous grid system of metallic fibers in continuous metal-to-metal contact.

However, no one has succeeded in producing synthetic fabric articles which are absorbent and at the same time prevent the buildup of static charges.

A need exists, therefore, for fabric articles which are essentially lint free, free of static electricity and highly absorbent. A specific need exists for toweling material which is highly absorbent, lint free and essentially static electrical charge free.

SUMMARY OF THE INVENTION

Accordingly, it is one object to the present invention to provide synthetic fabric articles which are essentially lint free, highly absorbent and free of static charges.

It is a further object of the present invention to provide a suitable toweling material for use in hospital operating rooms which is capable of absorbing aqueous media while at the same time exhibiting non-linting characteristics and no build up of static electrical charges.

These and other objects of the present invention which will become apparent from the following specification have been achieved through the use of a synthetic fabric material which has been treated to have a hydrophilic surface and which contains a conductive material interspersed therein.

DESCRIPTION OF PREFERRED EMBODIMENT

The fabric articles of the present invention can be constructed into any fabric from essentially any synthetic fiber or substrate including polyesters, polyolefins, polyamides, and acrylics as well as speciality fibers such as Nomex ® (an aromatic nylon fiber) and Kevlar ® (an aromatic polyamide fiber). Synthetic fibers can be of the continuous filament type or can be in the form of staples or other non-continuous forms. When the synthetic fiber is in the continuous filament form, the resulting fabric is essentially non-linting. When the synthetic fiber is in the non-continuous staple form, the fabric will lint to a limited extent but the amount of lint will be substantially less than that obtained by the corresponding cotton fabric. From experience, a properly constructed synthetic fabric having non-continuous filaments will exhibit linting characteristics less than that of cotton.

In order to render the resulting fabric conductive, it is necessary to introduce into the fabric a conductive species. One method for rendering fabric conductive is to introduce into the fabric, a minor amount of a conductive fiber. Typical conductive fibers included stainless steel, copper, platinum, gold, silver or the like. The conductive fiber can be constructed directly into the fabric. Carbon fibers can also be employed. If a carbon fiber is employed, it is preferred to wrap the carbon fiber around the synthetic fiber, however, this is not necessary.

The amount of conductive fiber in the fabric is a matter of choice. The use of large quantities of conductive fibers is not desirable since these will adversely affect the hand of the fabric and increase its cost. The use of too little conductive fiber will result in undesirable electrical charges. In general, the amount of conductive fiber should be selected so as to provide an effective degree of conductivity for a particular fabric and application. Satisfactory results have been obtained when the fabric comprises at least about 0.1% conductive fiber. A preferred range is from about 0.1 wt. % to about 2 wt. % of the conductive fiber. A more preferred range is from about 0.5% to 1.5 wt % with approximately 1% being preferred. The conductive fiber containing fabrics of the present invention demonstrate satisfactory antistatic properties as judged by standard NFP 99A or AATCC 76-82 test criterion.

Where the fabric article could come into contact with an open wound or incision on a patient it is desired that the conductive material be one which cannot be leached from the fabric into the wound. Thus, for hospital toweling, use of copper is not preferred since copper when in contact with the bodily fluids will tend to form copper ions which could enter into the patients body. Thus, platinum, gold, silver, carbon and stainless steel fibers are the preferred conductive materials for fabric articles which may come in contact with bodily fluids. From a cost stand point, carbon and stainless steel are the preferred conductive materials.

Since synthetic fibers are hydrophobic, it is necessary to treat the fabric with a treating process which will render the surface of the fabric hydrophilic. Numerous techniques have been suggested for rendering fabrics hydrophilic. Some techniques involve modifying the surface of the fabric to introduce small voids so as to physically trap the aqueous media into the fabric. Other techniques involving chemically modifying the surface of the fabric have been suggested in the patent literature, see for example U.S. Pat. Nos. 3,652,212, 4,242,408, 4,448,839 and 4,081,381. A polyester fabric under the trade name VISA exhibiting the necessary hydrophilic properties is sold by Milliken & Co., and fabric under the trade name SCOTCH RELEASE is sold by manufacturers using the 3M chemicals. The preferred techniques however, are those taught in U.S. Pat. No. 4,567,507 and pending U.S. application Ser. No. 426,498 U.S. Pat. No. 4,743,267, U.S. application Ser. No. 502,049 abandoned, U.S. application Ser. No. 663,103 U.S. Pat. No. No. 4,672,005 and U.S. application Ser. No. 788,059 U.S. Pat. No. 4,726,968 all commonly assigned and filed Sep. 29, 1982, Jun. 7, 1983, Oct. 22, 1984 and Oct. 16, 1985, respectively. These techniques have proven to be the most durable techniques for rendering fabrics hydrophilic. The techniques of U.S. application Ser. Nos. 426,488, 502,049 and 663,103 have proven to be especially durable and capable of withstanding numerous launderings without any degradation of the hydrophilic properties of the fabric. The other techniques which are available are generally less durable and upon repeated laundering can be removed leaving one with a hydrophobic fabric.

The present technique offers a substantial advantage to hospitals with respect to operating room fabric articles in general, and towels, in particular, not only because of reduced instances of infection but also because the higher durability and strength of the synthetic fabric itself should provide a toweling of substantially longer life than can be achieved with cotton toweling and also offers significant energy savings. This durability is important since hospitals utilize higher temperatures and stronger detergents than are utilized in typical laundering in order to both removed blood and other bodily fluids from the toweling and also to help disinfect the toweling to prevent cross infection between patients on subsequent uses.

The tightness of the construction and thickness of the fabric will depend upon its ultimate use. The fiber can be made into fabric using conventional techniques and equipment and no modification of the techniques is required.

The articles which can be prepared from the present fabric are any operating room articles which can be a source of wound contaminating lint, especially towels, surgical drapes, wound dressings, gowns for patients and operating room personnel, surgical masks, surgical packings, blankets, laparotomy sponges, surgical packings, etc.

Other features of the invention will become apparent in the course of the following descriptions of exemplary embodiments which are given for illustration of the invention and are not intended to be limiting thereof.

EXAMPLES

Example 1

A woven fabric towel was produced from double 150 denier continuous filament polyester. The polyester fibers were wrapped with 24 denier carbon fibers.

The results of a standard TDI No. 4 (Textile Distributors Institute) absorbency or wicking tests are shown in Table 1, comparing the carbon wrapped continuous filament polyester fibers of the present invention with standard cotton fabric. It can be seen from Table 1 that the fabric of the present invention exhibits superior wicking relative to conventional cotton toweling.

TABLE 1

| Rate of Absorbency (Wicking) According to TDI No. 4 | | | | | |
|---|---|---|---|---|---|
| Spun Polyester/Steel | | Cotton | | Continuous Filament Polyester/Carbon | |
| Warp | Filling | Warp | Filling | Warp | Filling |
| Test 1 | 4.5 | 6.5 | 5.5 | 4.4 | 7.0 | 7.0 |
| Test 2 | 4.2 | 7.0 | 5.5 | 5.0 | 7.5 | 6.7 |
| Test 3 | 4.5 | 7.0 | 4.5 | 5.0 | 6.7 | 6.0 |
| Average | 4.4 | 6.8 | 5.2 | 4.8 | 7.1 | 6.7 |

Example 2

A woven towel was produced from single weight 9.75/count warp yarn comprising 99 wt % polyester and 1 wt % steel. The fabric was produced using single weight filling, spun yarn comprising 9.40 count fibers having the same composition as the warp yarn. An operating room towel was constructed from this fabric with a weaving construction of 73×25.

The results of a standard absorbency or wicking test comparing the spun polyester/steel fabric of the present invention to standard cotton toweling are shown in Table 1. Again, the fabric of the present invention exhibits absorbency characteristics equal to or superior to conventional cotton toweling.

The present fabric while specially suitable for operating room towels will find use in other applications as well. For example, hospital gowns, blankets, sheets, washcloths and even drapes can be advantageously produced from the present fabric. Since cleanliness is essential to reducing and eliminating infections in surgical patients, it is necessary that all the articles which come in contact with the patients either be easily cleaned or be disposable. Generally speaking synthetic fabrics are difficult to launder because of their hydrophobic nature. The present fabric because it is hydrophilic is generally easily laundered and exhibits excellent soil release properties. The non-static nature of the present product means that it can be safely used in environments where gases, such as ether or oxygen, are in use where normal synthetic fabrics could not be employed at all. The long life of the fabric articles of the present invention results in an overall cost savings to the medical establishments since it is not necessary to replace gowns; toweling and other material as often when these materials are prepared from a synthetic fiber rather than from a cotton fiber. The durability and strength of synthetic fabrics as compared with cotton has long been recognized, the present invention allows hospitals to take more advantage of these characteristics of synthetic fabrics than has been previously possible.

The fabric of the present invention in addition to being useful to medical establishments can also be used in other applications where a non-linting or reduced linting fabric having good absorbing capability and no buildup static charge is required.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A non-linting, anti-static, aqueous media absorbent operating room fabric article, comprising:
    a synthetic fabric fiber substrate, wherein said synthetic fabric fiber substrate is chemically treated to render it absorbent to aqueous media; and
    an anti-statically effective amount of a conductive fiber consisting essentially of a fiber selected from the group consisting of stainless steel, copper, platinum, gold, silver and carbon fibers, in combination with said substrate fiber.

2. The fabric article of claim 1, wherein said synthetic substrate is a member selected from the group consisting of polyesters, polyolefins, polyamides and acrylics.

3. The fabric article of claim 1, comprising at least about 0.1 wt. % conductive fiber.

4. The fabric article of claim 3, comprising about 0.1 to about 2.0 wt. % of said conductive fiber.

5. The fabric article of claim 4, comprising 0.5-1.5 wt % of said conductive fiber.

6. The fabric article of claim 1, wherein said fabric article is a member selected from the group consisting of operating room towels, surgical drapes, surgical gowns, blankets, sheets, laparotomy sponges, surgical packings, patient gowns and washcloths.

7. An operating room fabric article, comprising:
    a synthetic fabric fiber substrate, wherein said synthetic fabric fiber substrate is chemically treated to render it absorbent to aqueous media; and
    an anti-statically effective amount of a conductive fiber consisting essentially of a fiber selected from the group consisting of stainless steel, copper, platinum, gold, silver and carbon fibers, wherein said fabric article is woven from said substrate fiber and said conductive fiber.

8. The fabric article of claim 1, wherein said conductive fiber is in the continuous filament form.

9. The fabric article of claim 1, wherein said conductive fiber is in the staple fiber form.

10. The fabric article of claim 1, wherein said conductive fiber is wrapped around said substrate fiber.

11. The fabric article of claim 10, wherein said conductive fiber is carbon fiber.

12. The fabric article of claim 1, wherein said synthetic fabric fiber substrate is polyester.

13. The fabric article of claim 12, wherein said synthetic fabric fiber substrate is polyester and said conductive fiber is stainless steel.

* * * * *